United States Patent
Egler et al.

(10) Patent No.: US 11,065,434 B2
(45) Date of Patent: Jul. 20, 2021

(54) BLOOD PUMP WITH IMPELLER RINSE OPERATION

(71) Applicant: HeartWare, Inc., Miami Lakes, FL (US)

(72) Inventors: Mark S. Egler, Reading, MA (US); Fernando Casas, Miami Lakes, FL (US); Carlos Reyes, Davie, FL (US); Jeffrey A. Larose, Raleigh, NC (US)

(73) Assignee: HeartWare, Inc., Miami Lakes, FL (US)

( * ) Notice: Subject to any disclaimer, the term of this patent is extended or adjusted under 35 U.S.C. 154(b) by 109 days.

(21) Appl. No.: 16/199,684

(22) Filed: Nov. 26, 2018

(65) Prior Publication Data
US 2019/0167874 A1    Jun. 6, 2019

Related U.S. Application Data

(60) Provisional application No. 62/594,697, filed on Dec. 5, 2017.

(51) Int. Cl.
| | | |
|---|---|---|
| *A61M 60/40* | (2021.01) | |
| *A61M 60/50* | (2021.01) | |
| *A61M 60/82* | (2021.01) | |
| *A61M 60/148* | (2021.01) | |
| *A61M 60/824* | (2021.01) | |

(52) U.S. Cl.
CPC .......... *A61M 60/40* (2021.01); *A61M 60/148* (2021.01); *A61M 60/50* (2021.01); *A61M 60/82* (2021.01); *A61M 60/824* (2021.01)

(58) Field of Classification Search
None
See application file for complete search history.

(56) References Cited

U.S. PATENT DOCUMENTS

| | | | | |
|---|---|---|---|---|
| 4,944,748 A | * | 7/1990 | Bramm ................. | F04D 13/06 416/111 |
| 5,208,522 A | * | 5/1993 | Griepentrog ........... | F01D 15/10 318/611 |
| 5,385,581 A | * | 1/1995 | Bramm ................. | F04D 13/06 417/356 |

(Continued)

FOREIGN PATENT DOCUMENTS

| | | |
|---|---|---|
| WO | 2014133942 A1 | 9/2014 |
| WO | 2016130944 A1 | 8/2016 |

OTHER PUBLICATIONS

International Search Report and Written Opinion dated Feb. 28, 2019, for corresponding International Application No. PCT/US2018/062431; International Filing Date: Nov. 26, 2018 consisting of 14 pages.

*Primary Examiner* — Carl H Layno
*Assistant Examiner* — Manolis Y Pahakis
(74) *Attorney, Agent, or Firm* — Christopher & Weisberg, P.A.

(57) ABSTRACT

A method of operating an implantable blood pump having a first stator, a second stator, and an impeller movably disposed there between. The method includes applying a first voltage waveform at first phase to the first stator to generate a magnetic field to rotate the impeller. A second voltage waveform is applied at a second phase shifted from the first phase to the second stator to rotate the impeller, the second voltage waveform is asymmetric to the first voltage waveform.

9 Claims, 5 Drawing Sheets

(56) References Cited

U.S. PATENT DOCUMENTS

| | | | | |
|---|---|---|---|---|
| 6,227,817 | B1 * | 5/2001 | Paden | F04D 13/0646 |
| | | | | 417/356 |
| 6,264,635 | B1 * | 7/2001 | Wampler | H02K 7/09 |
| | | | | 604/151 |
| 6,293,901 | B1 * | 9/2001 | Prem | F04D 29/048 |
| | | | | 600/17 |
| 6,688,861 | B2 | 2/2004 | Wampler | |
| 7,575,423 | B2 | 8/2009 | Wampler | |
| 7,976,271 | B2 | 7/2011 | Larose et al. | |
| 8,419,609 | B2 | 4/2013 | Shambaugh, Jr. et al. | |
| 8,512,013 | B2 | 8/2013 | Larose et al. | |
| 9,638,202 | B2 * | 5/2017 | Ozaki | A61M 1/101 |
| 2003/0164654 | A1 * | 9/2003 | Thaxton | F16C 32/0459 |
| | | | | 310/90.5 |
| 2006/0247486 | A1 * | 11/2006 | Mendler | F04D 13/064 |
| | | | | 600/16 |
| 2011/0238172 | A1 * | 9/2011 | Akdis | F04D 13/0666 |
| | | | | 623/3.11 |
| 2012/0169167 | A1 * | 7/2012 | Fan | F16C 32/0478 |
| | | | | 310/90.5 |
| 2014/0241904 | A1 * | 8/2014 | Yanai | F04D 1/00 |
| | | | | 417/53 |
| 2016/0199556 | A1 * | 7/2016 | Ayre | A61M 1/122 |
| | | | | 600/16 |
| 2016/0235899 | A1 * | 8/2016 | Yu | A61M 1/1015 |
| 2017/0340788 | A1 * | 11/2017 | Korakianitis | A61M 1/107 |
| 2018/0369466 | A1 * | 12/2018 | Nestler | A61M 1/122 |

* cited by examiner

BLOOD PUMP WITH IMPELLER RINSE OPERATION

CROSS-REFERENCE TO RELATED APPLICATION

This application claims the benefit of U.S. Application Ser. No. 62/594,697, filed Dec. 5, 2017.

FIELD

The present technology is generally related to a method and system for moving the impeller of an implantable blood pump to order to increase washing of the impeller surfaces.

BACKGROUND

Implantable blood pumps used as a mechanical circulatory support devices or "MCSDs" include a pumping mechanism to move blood from the heart out to the rest of the body. The pumping mechanism may be a centrifugal flow pump, such as the HVAD® Pump manufactured by HeartWare, Inc. in Miami Lakes, Fla., USA. The HVAD® Pump is further discussed in U.S. Pat. No. 8,512,013, the disclosure of which is hereby incorporated herein in its entirety. In operation, the blood pump draws blood from a source such as the right ventricle, left ventricle, right atrium, or left atrium of a patient's heart and impels the blood into an artery such as the patient's ascending aorta or peripheral artery.

In an exemplary HVAD® pump, an impeller is positioned within a housing having an upstream inflow cannula and a downstream outlet. The impeller is configured to rotate along an axis defined by the rotor and to impel blood upstream from the inflow cannula downstream to the outlet. In such a configuration, the impeller pumps blood in a direction substantially perpendicular to the axis about which it rotates. Dual stators are included in the pump, one upstream of the impeller and one downstream from the impeller and are each configured to rotate the impeller to impel blood. Disposed between the impeller and each respective stator is a non-ferromagnetic ceramic disk that separates the respective stator from the impeller and provides a smooth surface to pump blood. However, owing to the small gap between each ceramic disk and the impeller, the risk of thrombus is potential stagnation of blood proximate the ceramic disk.

SUMMARY

The techniques of this disclosure generally relate to a method and system for moving the impeller of an implantable blood pump to order to increase washing of the impeller surfaces.

In one aspect, the present disclosure provides a method of operating an implantable blood pump having a first stator, a second stator, and an impeller movably disposed there between. The method includes applying a first voltage waveform at first phase to the first stator to generate a magnetic field to rotate the impeller. A second voltage waveform is applied at a second phase shifted from the first phase to the second stator to rotate the impeller, the second voltage waveform is asymmetric to the first voltage waveform.

In another aspect, the first voltage waveform is a square wave.

In another aspect, the second voltage waveform is a square wave.

In another aspect, second voltage waveform is trapezoidal.

In another aspect, the first voltage waveform is applied while the impeller is rotating.

In another aspect, the first voltage waveform and the second voltage waveform each have transition steps between positive and negative polarities of their respective waveforms, and wherein the first voltage waveform and the second voltage waveform each have the same polarity at their respective transition steps.

In another aspect, the duration of the transition steps of the first voltage waveform and the second voltage waveform range from 1-30 electrical degrees.

In another aspect, the application of the first voltage waveform and the second voltage waveform moves the impeller axially.

In another aspect, during operation of the implantable blood pump, a predetermined axial gap is maintained between the impeller and the first stator, and wherein the application of the first voltage waveform and the second voltage waveform temporarily increases the predetermined axial gap.

In one aspect, the disclosure provides a controller for an implantable blood pump having a first stator, a second stator, and an impeller movably disposed there between, the controller includes a control circuit configured to apply a first voltage waveform at first phase to the first stator to generate a magnetic field to rotate the impeller for a first period of time and apply a second voltage waveform phase shifted from the first phase to the second stator to rotate the impeller during the first period of time, the second voltage waveform being asymmetric to the first voltage waveform.

In another aspect, the control circuit is further configured to delay the application of the second voltage waveform by 60 degrees.

In another aspect, the first voltage waveform is a square wave.

In another aspect, the second voltage waveform is a square wave.

In another aspect, the second voltage waveform is trapezoidal.

In another aspect, the first period of time occurs while the impeller is rotating.

In another aspect, the control circuit is further configured to apply the first voltage waveform and the second voltage waveform during a second period of time different than the first period of time, and wherein during the second period of time, the first phase and the second phase are the same, and the first voltage waveform and the second voltage waveform are symmetric.

In another aspect, the application of the first voltage waveform and the second voltage waveform moves the impeller axially.

In another aspect, during operation of the implantable blood pump, a predetermined axial gap is maintained between the impeller and the first stator, and wherein the application of the first voltage waveform and the second voltage waveform temporarily increases the predetermined axial gap.

In one aspect, a method of operating an implantable blood pump having a first stator, a second stator, and an impeller movably disposed there between comprises applying a first voltage waveform at first phase to the first stator to generate a magnetic field to rotate the impeller and applying a second voltage waveform at a second phase shifted from the first phase to the second stator to rotate the impeller, the second voltage waveform being asymmetric to the first voltage waveform, the first voltage waveform and the second voltage waveform each having transition steps between positive and negative polarities of their respective waveforms, and the first voltage waveform and the second voltage waveform each have the same polarity at their respective transition steps. During operation of the implantable blood pump, a predetermined axial gap is maintained between the impeller and the first stator, and wherein the application of the first voltage waveform and the second voltage waveform temporarily increases the predetermined axial gap.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Before describing in detail exemplary embodiments, it is noted that the embodiments reside primarily in combinations of apparatus components and processing steps related to axially moving an impeller of a blood pump during operation. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
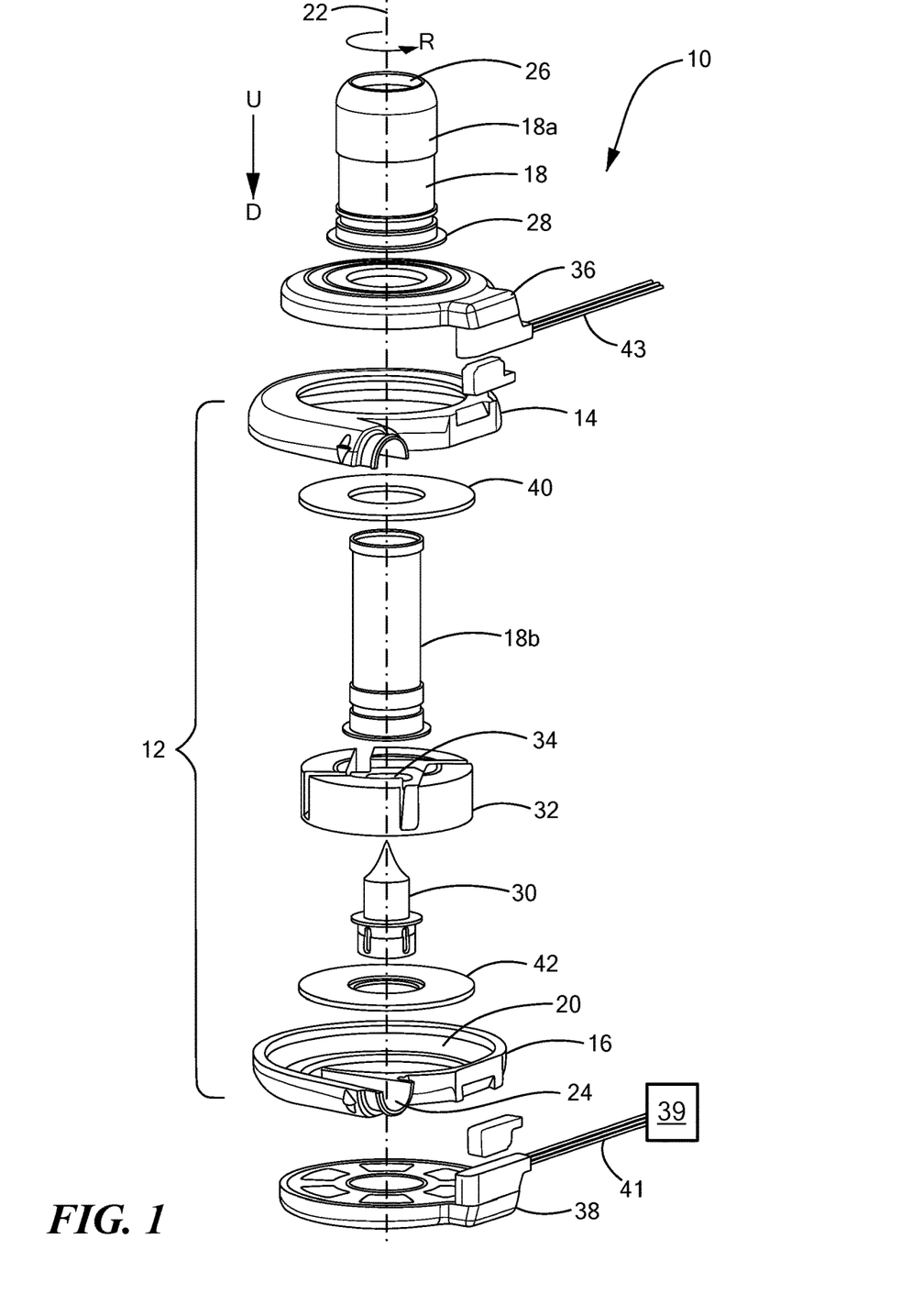
FIG. 1 is an exploded view of an exemplary blood pump constructed in accordance of the principles of the present application.

Referring now to the drawings in which like reference designators refer to like elements there is shown in FIG. 1 an exemplary blood pump constructed in accordance with the principles of the present application and designated generally "10." The blood pump 10 according to one embodiment of the disclosure includes a static structure or housing 12 which houses the components of the blood pump 10. In one configuration, the housing 12 includes a upper housing or first portion 14, a lower housing or second portion 16, and an inlet portion or inflow cannula 18 which includes an outer tube 18a and an inner tube 18b. The first portion 14 and the second portion 16 cooperatively define a volute shaped chamber 20 having a major longitudinal axis 22 extending through the first portion 14 and inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls.

Figure 2:
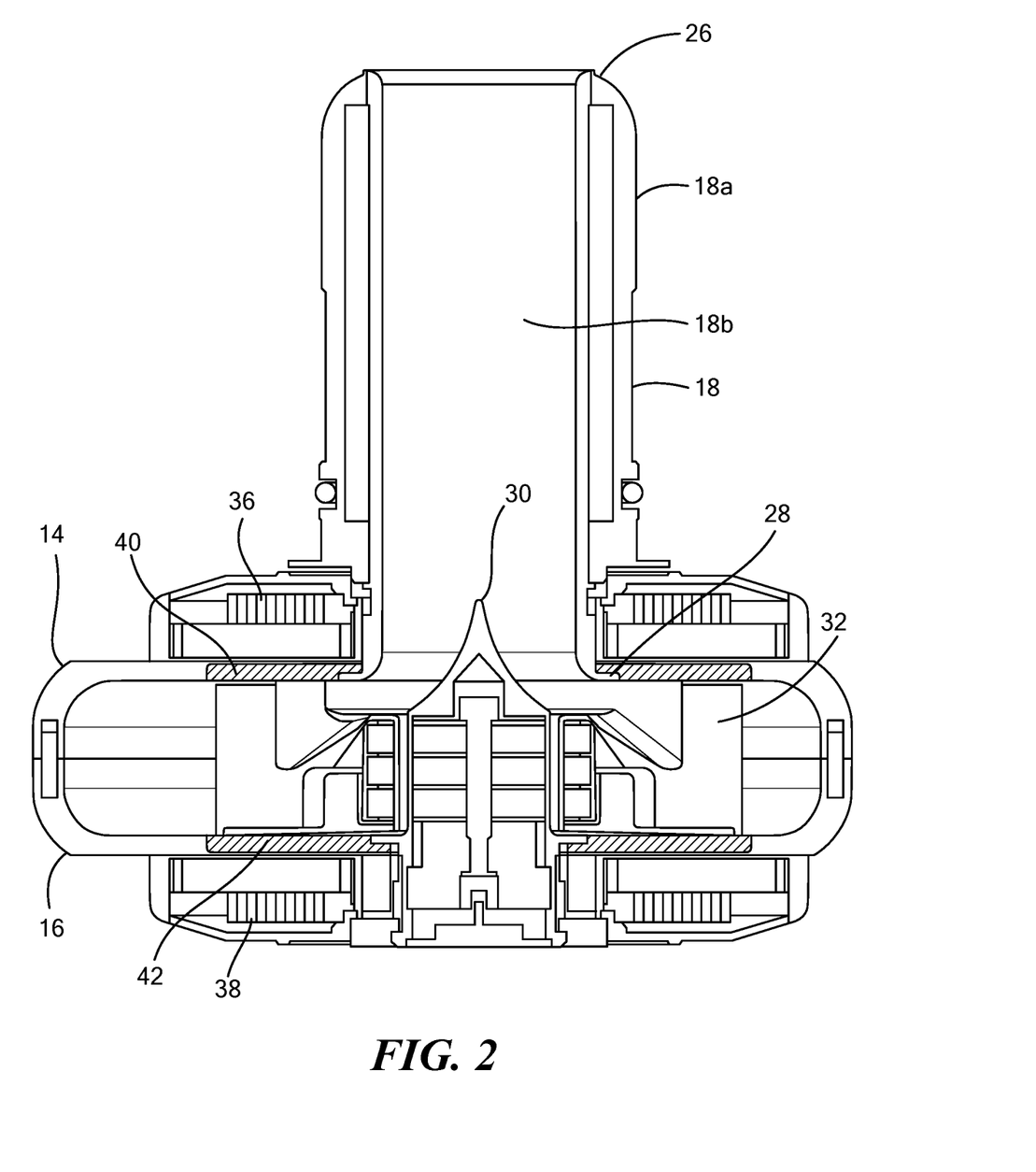
FIG. 2 is cross-sectional view of the assembled blood pump shown in FIG. 1.

Referring now to FIGS. 1 and 2, the inflow cannula 18 is generally cylindrical and extends from first portion 14 and extends generally along axis 22. The inflow cannula 18 has an upstream end or proximal end 26 remote from second portion 16 and a downstream end or distal end 28 proximate the chamber 20. The parts of the housing 12 mentioned above are fixedly connected to one another so that the housing 12 as a whole defines a continuous enclosed flow path. The flow path extends from upstream end 26 at the upstream end of the flow path to the outlet 24 at the downstream end of the flow path. The upstream and downstream directions along the flow path are indicated in FIG. 1 by the arrows U and D respectively. A post 30 is mounted to second portion 16 along axis 22. A generally disc shaped ferromagnetic rotor 32, for example, and impeller with a central hole 34, is mounted within chamber 20 for rotation about the axis 22. Rotor 32 includes a plurality of permanent magnets and also includes flow channels for transferring blood from adjacent the center of the rotor 32 to the periphery of the rotor 32. In the assembled condition, post 30 is received in the central hole of the rotor 32. A first stator 36 having a plurality of coils may be disposed within the first portion 14 upstream from the rotor 32. The first stator 36 may be axially aligned with the rotor along axis 22 such that when a current is applied to the plurality of coils in the first stator 36, the electromagnetic forces generated by the first stator 36 rotate the rotor 32 and pump blood. A second stator 38 may be disposed within the second portion 16 downstream from the rotor 32. The second stator 38 may be configured to operate in conjunction with or independently of the first stator 36 to rotate the rotor 32.

Electrical connectors 41 and 43 (FIG. 1) are provided on the first portion 14 and the second portion 16 respectively for connecting the coils to a common source of power such as a controller 39, shown connected to connector 41, but is also connected to the pump by connector 43. The controller 39 is arranged and configured to apply power to the coils of the pump to create a rotating magnetic field which spins rotor 32 around axis 22 in a predetermined first direction of rotation, such as the direction R indicated by the arrow in FIG. 1, i.e., counterclockwise as seen from the upstream end of inflow cannula 18. In other configurations of the blood pump 10, the first direction may be clockwise. Rotation of the rotor 32 impels blood downstream along the flow path so that the blood moves in a downstream direction D along the flow path, and exits through the outlet 24. During rotation, hydrodynamic and magnetic bearings (not shown) support the rotor 32 and maintain the rotor 32 out of contact with the surfaces of the elements of the first portion 14 and the second portion 16 during operation. A first non-ferromagnetic disk 40 may be disposed within the first portion 14 upstream from the rotor 32 between the first stator 36 and the rotor 32 and a second non-ferromagnetic disk 42 may be disposed downstream from the rotor 32 within the second portion 16 between the second stator 38 and the rotor 32. The general arrangement of the components described above may be similar to the blood pump 10 used in the mechanical circulatory support device ("MCSD") sold under the designation HVAD by HeartWare, Inc., assignee of the present application. The arrangement of components such as the magnets, electromagnetic coils, and hydrodynamic bearings used in such a pump and variants of the same general design are described in U.S. Pat. Nos. 6,688,861; 7,575,423; 7,976,271; and 8,419,609, the disclosures of which are hereby incorporated by reference herein.

Figure 3:
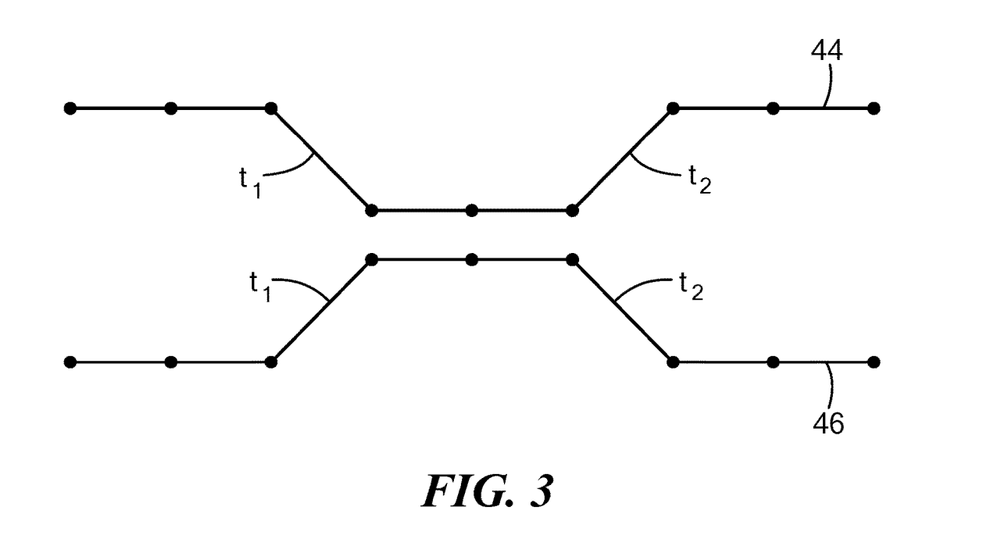
FIG. 3 is a diagram showing symmetric voltage trapezoidal waveforms applied to each respective stator during normal operation.

Referring now to FIG. 3, while the rotor 32 is rotating between the first stator 36 and the second stator 38, the controller 39 applies a first voltage waveform 44 to the first stator 36 and a second voltage waveform 46 to the second stator 38. Each of the first voltage waveform 44 and the second voltage waveform 46 provide power to rotate the impeller 32 independently of the other stator while the impeller is rotating after a startup sequence is initiated. In the exemplary configuration shown in FIG. 3, the first voltage waveform 44 is equal to and symmetric with the second voltage waveform 46 such that the net axial force on the impeller 32 is zero. In the configuration shown in FIG. 3, the first and second voltage waveforms define trapezoidal waveforms with sloped transitions applied at the same phase. As used herein, the transition step of each waveform described herein refers to portions of the respective waveforms in which the voltage transitions from a positive voltage to a negative voltage polarity or vice-versa. As shown in FIG. 3, the slope of the transition portions ("$t_1$" or "$t_2$") of the first and second voltage waveforms are equal, which creates a zero net axial force on the impeller 32.

Figure 4:
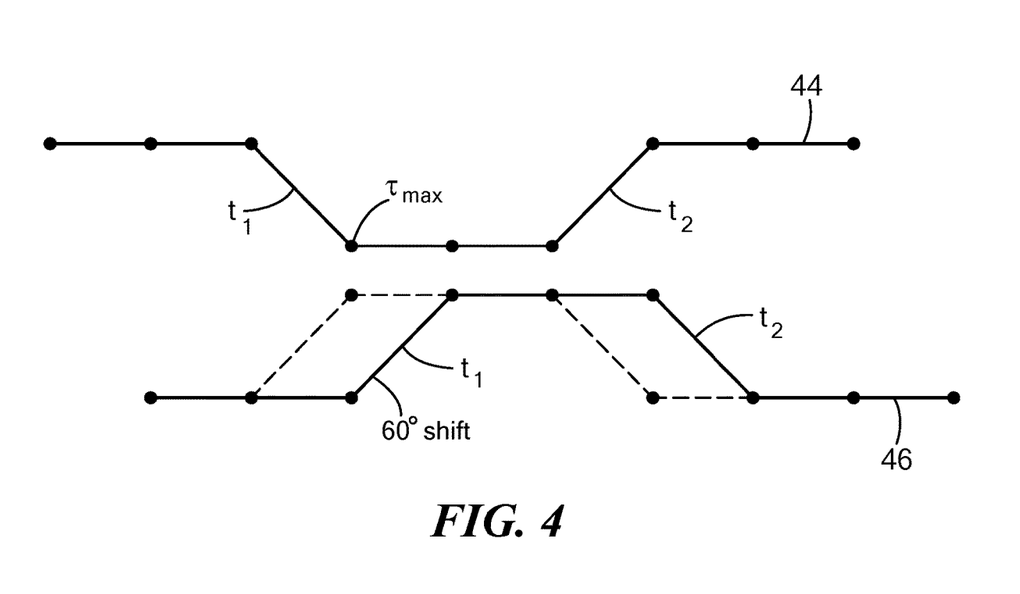
FIG. 4 is a diagram showing the voltage waveforms shown in FIG. 3 with the second voltage waveform phase shifted 60 degrees.

Referring now to FIG. 4, in another configuration, the second voltage waveform 46 is delayed or otherwise phase shifted 60 degrees from the configuration shown in FIG. 3 while both waveforms are trapezoidal. Although shown phase shifted 60 degrees, the second voltage waveform 46 may be phase shifted between 1-90 degrees in other configurations. As shown in FIG. 4, owing to the second voltage waveform 46 being phased shifted by 60 degrees (illustrated by showing the in-phase transition in dashed lines), when the first voltage waveform 44 is at its maximum torque angle ($\tau_{max}$) with respect to the second voltage waveform 46 of the second stator 38, the impeller 32 is temporarily axially displaced toward the second stator 38.

Figure 5:
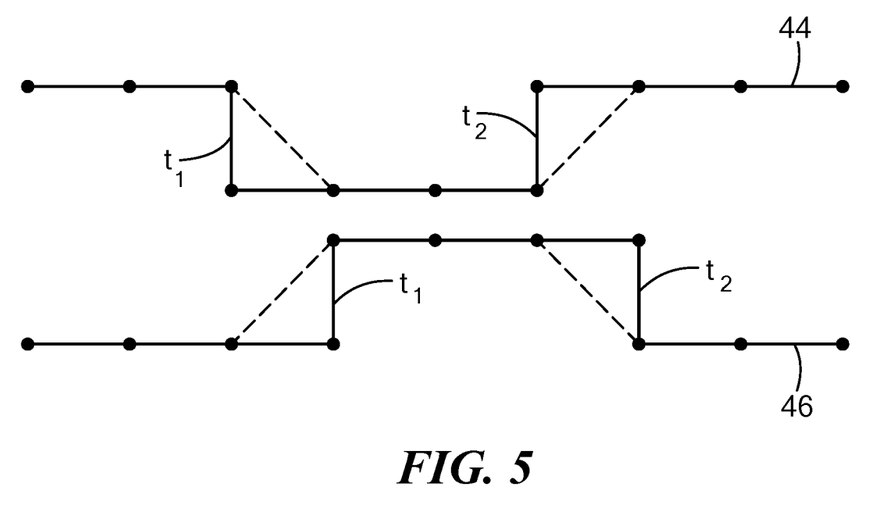
FIG. 5 is a diagram showing asymmetric square voltage waveforms applied to each respective stator with each transition having the same polarity.

Referring now to FIG. 5, in another configuration, the first voltage waveform 44 and the second voltage waveform 46 define square waves that are in phase, but asymmetric. In this configuration, the first voltage waveform 44 and the second voltage waveform 46 have the same polarity during transitions steps. That is, rather than sloped transitions, the transitions may be substantially instantaneous. The net effect of both the first voltage waveform 44 and the second voltage waveform 46 during transition steps is to place on the impeller 32 a net axial force, either toward the first stator 36 or toward the second stator 38 depending on the polarity during the transition step similar to the result of the phase delay described with respect to the configuration shown in FIG. 4. In the configuration shown in FIG. 5, the net axial force on the impeller 32 at $t_1$ or waveform 44 is toward the second stator 38.

Figure 6:
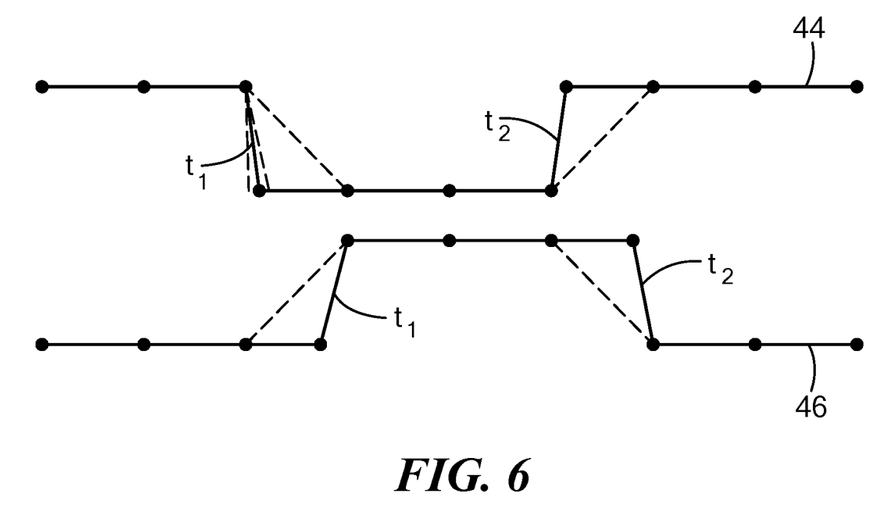
FIG. 6 is a diagram showing the voltage waveforms shown in FIG. 5 with reduced slopes during transitions.

Referring now to FIG. 6, in a similar configuration to that shown in FIG. 5, the transitions are sloped similar to the square wave formation for the first voltage waveform 44 and the second voltage waveform 46, however the transitions are less steep, as indicated by the dashed lines adjacent $t_1$. That is, instead of a 90 degree transition, the slopes of the respective transitions are less steep using, for example, pulse width modulation. As shown in FIG. 6, the durations of the transitions for the first voltage waveform 44 and the second voltage waveform 46 are not zero, but extended to produce quieter running of the motor and still provides for axial movement of the impeller 32. For example, the durations of transitions "$t_1$" in FIG. 6 of the first voltage waveform 44 and the second voltage waveform 46 may range from, for example, 1-30 electrical degrees to reduce acoustic noise.

Figure 7:
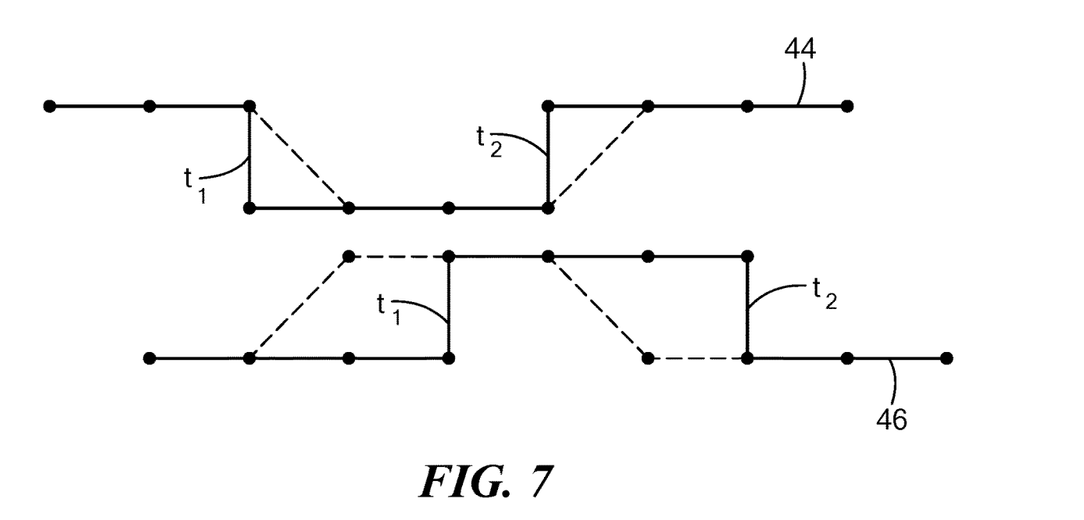
FIG. 7 is a diagram showing the asymmetric square voltage waveforms applied to each respective stator with the second voltage waveform phase shifted 60 degrees.

Referring now to FIG. 7, in a similar configuration to that shown in FIG. 5, the first voltage waveform 44 and the second voltage waveform 46 are asymmetric square waves, however, the second voltage waveform 46 is phase shifted, or otherwise delayed 60 degrees from the first voltage waveform 44. In this configuration, the first voltage waveform 44 provides more torque on the impeller 32, is in sync with the impeller 32, and provides an axial force on the impeller 32 toward the second stator 38. The second voltage waveform 46 provides less torque on the impeller 32, but provides axial force toward the second stator 38.

Figure 8:
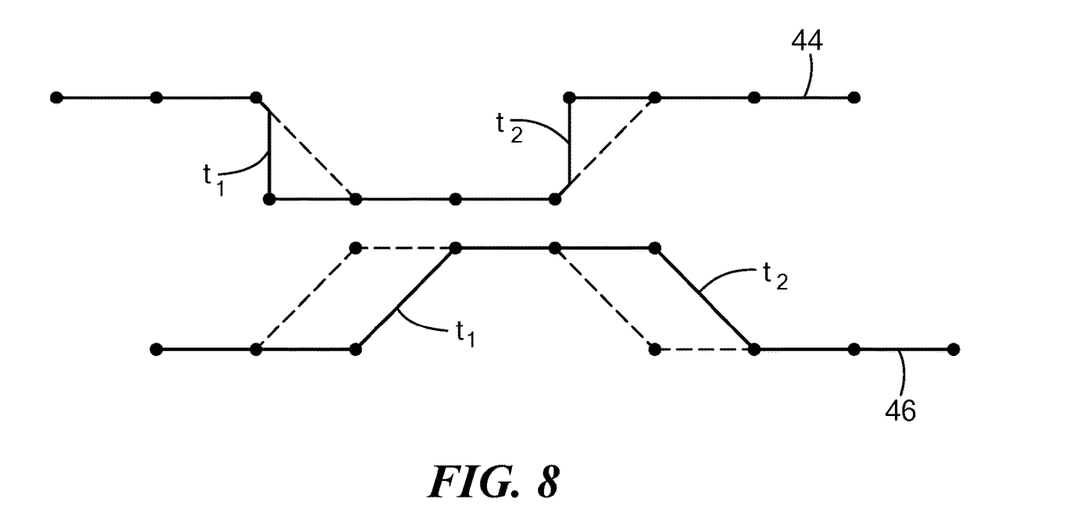
FIG. 8 is a diagram showing the first voltage waveform as substantially square waveform with a partially reduced slope during transition and a phase shifted by 60 degrees trapezoidal second voltage waveform.

Referring now to FIG. 8, in another configuration, first voltage waveform 44 is substantially square with a portion of the transition sloped less steep as to reduce the axial force on the impeller 32. The second voltage waveform 46 is phase shifted by 60 degrees but still trapezoidal as to reduce acoustics.

In any of the configurations discussed above with a net axial force on the impeller 32, the application of particular first and second voltage waveforms may be programmed by the controller 39 for a predetermined period of time. For example, the controller 39 may apply the first and second voltage waveforms shown in FIG. 3 during normal operation that apply no net axial force on the impeller 32 for a first predetermined period of time. The first and second voltage waveforms that apply a net axial force on the impeller 32 may be applied during a second period of time as part of a rinse mode of operation. For example, the application of a net axial force on the impeller 32 may cause the impeller to momentarily be axially moved by, for example, a thousandth of an inch toward the second stator 38. This momentary axial movement of the impeller 32 may increase a washing effect and cause thrombus to be dislodged from the surface of the impeller 32, or create a larger axial gap between the impeller 32 and the respective ceramic disks such that larger thrombus particles may be moved through the pump. In an exemplary configuration, during normal operation of the pump 10, a predetermined axial gap is 1 thousandth of an inch between disk 40 and the impeller 32. By application of the first and second voltage waveforms shown for example in FIG. 5, for example, every 15 seconds in between the normal operation shown in FIG. 3, the impeller 32 may momentarily move axially toward disk 42 which may double the axial gap between the impeller and disk 40.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

What is claimed is:

1. A method of operating an implantable blood pump having a first stator, a second stator, and an impeller movably disposed between the first stator and the second stator, wherein the first stator is located upstream of the impeller, the method comprising:
   applying a first voltage waveform at a first time of operation of the blood pump to the first stator to generate a magnetic field to rotate the impeller;
   applying a second voltage waveform during the first time to the second stator to rotate the impeller, the second voltage waveform being symmetric to the first voltage waveform, wherein the second voltage waveform has a transition portion that has a same polarity as a respective transition portion of the first voltage waveform;
   wherein applying the first and second voltage waveforms includes producing a zero net axial force on the impeller, thereby maintaining a predetermined axial gap between the impeller and the first stator during the first time;
   applying the first voltage waveform at a second time of operation of the blood pump to the first stator to generate a magnetic field to rotate the impeller, the second time being later than the first time of operation of the blood pump;
   changing the second voltage waveform applied to the second stator and rotating the impeller during the second time of operation, so that the second voltage waveform becomes asymmetric to the first voltage waveform; and
   wherein applying the first voltage waveform and the second voltage waveform includes temporarily increasing the predetermined axial gap when the first voltage waveform is at a maximum torque angle with respect to the second voltage waveform, thereby increasing a rinsing effect on a surface of the impeller during a portion of the second time of operation of the implantable blood pump.

2. The method of claim 1, wherein applying the second voltage waveform includes phase delaying the application of the second voltage by 60 degrees after application of the first voltage waveform.

3. The method of claim 1, wherein the first voltage waveform is a square wave.

4. The method of claim 1, wherein the second voltage waveform is a square wave.

5. The method of claim 1, wherein the second voltage waveform is trapezoidal.

6. The method of claim 1, wherein applying the first voltage waveform includes applying the first voltage waveform while the impeller is rotating.

7. The method of claim 1, wherein the first voltage waveform and the second voltage waveform each have transition steps between positive and negative polarities of their respective waveforms, and wherein the first voltage waveform and the second voltage waveform each have the same polarity at their respective transition steps.

8. The method of claim 7, wherein the duration of the transition steps of the first voltage waveform and the second voltage waveform range from 1-30 electrical degrees.

9. The method of claim 1, further including moving the impeller axially during the application of the first voltage waveform and the second voltage waveform.

\* \* \* \* \*